United States Patent [19]

Ullman et al.

[11] 4,121,975

[45] Oct. 24, 1978

[54] PRETREATMENT OF SAMPLES FOR POLYIODOTHYRONINE ASSAYS

[75] Inventors: Edwin F. Ullman, Atherton; Joel E. Lavine, Mountain View, both of Calif.

[73] Assignee: Syva Company, Palo Alto, Calif.

[21] Appl. No.: 716,032

[22] Filed: Aug. 20, 1976

[51] Int. Cl.$^2$ .................... G01N 33/00; G01N 31/00; G01N 31/14

[52] U.S. Cl. .................................. 195/99; 23/230 B; 195/103.5 A; 424/12

[58] Field of Search ................. 195/103.5 R, 103.5 A, 195/99; 23/230 B; 424/12

[56] References Cited

U.S. PATENT DOCUMENTS

| 3,850,577 | 11/1974 | Ashkar | 23/230 B |
| 3,928,553 | 12/1975 | Hollander | 23/230 B |
| 3,955,925 | 5/1976 | Proksch et al. | 23/230 B |

OTHER PUBLICATIONS

Griffith et al., Advan. Catal. Related Subjs. 23, 209 (1973).

Primary Examiner—Alvin E. Tanenholtz
Assistant Examiner—C. A. Fan
Attorney, Agent, or Firm—Townsend and Townsend

[57] ABSTRACT

Composition and method are provided for the pretreatment of serum prior to a thyroxine assay. Prior to carrying out of the assay, particularly an immunoassay or competitive protein-binding assay, the serum sample is combined with cyclodextrin preferably in combination with an hydroxylated aromatic carboxylic acid in a basic medium, in amounts sufficient to minimize interference with obtaining an accurate and reliable determination of polyiodothyronine in the serum. Normally, after the reagents have been added to the serum, a small incubation period is allowed, after which time the additional reagents may be added for carrying out the assay.

11 Claims, No Drawings

PRETREATMENT OF SAMPLES FOR POLYIODOTHYRONINE ASSAYS

BACKGROUND OF THE INVENTION

1. Field of the Invention

The body's maintenance of normal thyroxine is an important factor in good health. Since many ailments can be attributed to an enhanced or diminished concentration (hyperthyroid or hypothyroid), the determination of thyroxine in blood samples has become a common occurrence. There are a number of different techniques which can be employed for the determination of thyroxine. The more accurate assays depend upon specific protein recognition for thyroxine. By providing a competition between a tagged thyroxine and the thyroxine for a specific binding protein, the amount of the tagged material which becomes bound to the protein or remains free can be correlated with the amount of thyroxine in the serum.

Thyroxine is a highly functionalized compound and is also very hydrophobic. Thyroxine is therefore capable of binding both specifically and non-specifically to a wide variety of proteins. In addition, its ability to bind specifically to proteins can be affected by a number of different materials, e.g. surfactants.

The existence of various naturally occurring materials which interfere with the accuracy of results obtained in thyroxine assays is a serious problem. First, standards are normally run with known amounts of thyroxine which may not have the interferants. The results obtained with the serum samples will therefore differ from the standards. In addition, correlations between different techniques for thyroxine determination cannot be made, since the various interferants may interfere differently with the different techniques. Finally, since individuals will vary as to the amount of the interferants present in their serum, even from day to day, no reliable comparison can be made of the results. It is therefore essential that a thyroxine assay take account of the presence of the interferants and either remove the interferants, deactivate their effect, or be able quantitatively to account for their presence.

BRIEF DESCRIPTION OF THE PRIOR ART

Sc. J. Clin. Invest. 35 649 (1975) describes the effect of fatty acids on serum thyroxine determinations by competitive protein-binding radioassay. Griffith and Bender, Advan. Catal. Related Subjs. 23 209 (1973) report that cyclodextrin complexes with fatty acids. Salicylate is known to displace thyroxine from albumins and TBPA as reported by Laisen, et al, J. Clin. Endocrinal, Metab. 37 177 (1973). See also, Ramados, et al., J. Biol. Chem. 251, 98 (1976). Application Ser. No. 644,408, filed Dec. 29, 1975, describes a homogeneous enzyme immunoassay for thyroxine.

SUMMARY OF THE INVENTION

Method and composition are provided for serum pretreatment prior to polyiodothyronine, particularly thyroxine, determination, where the accuracy and the reliablility of the determination is affected by the presence of natural proteins and/or lipemic compositions e.g. free fatty acid (FFA). Cyclodextrin, particularly α-cyclodextrin, perferably as an alkaline aqueous solution, particularly in combination with a protein releasing agent, is combined with the serum for a time sufficient to inhibit any interferants. The resulting composition may then be used in accordance with known techniques for a polyiodothyronine determination.

DESCRIPTION OF THE SPECIFIC EMBODIMENTS

In accordance with the subject invention, cyclodextrin, either α- or β-, preferably α, preferably as an alkaline aqueous solution in combination with a protein releasing agent, e.g., an hydroxylated aromatic carboxylic acid, e.g. salicylic acid is provided to be combined with serum samples for the determination of polyiodothyronine.

Since α-cyclodextrin is preferred, only α-cyclodextrin will be referred to in the remainder of the specification. β-Cyclodextrin may be used in place of α-cyclodextrin, but since it is generally less effective, the amount employed will generally be in the higher portion of the range. The polyiodothyronines of interest are T-4 and T-3, particularly T-4 (thyroxine) and T-4 will be used as illustrative of the polyiodothyronines of from three to four iodine groups.

When employing the α-cyclodextrin, various protocols may be employed to provide advantages in addition to the improvement provided by the addition of α-cyclodextrin. For release from protein, acid or base can be used or ethanol extraction can be used. However, α-cyclodextrin is acid labile and ethanol insoluble, so that use of acid and ethanol requires additional sample treatment to permit the use of α-cyclodextrin. Therefore, the preferred method is to use α-cyclodextrin in combination with base.

The concentration of α-cyclodextrin will be sufficient to provide from about 0.1–5, preferably from about 1.5–4 weight percent of the mixture. The reagent solution when base is employed will provide a base normality after mixing with the sample in the range of about 0.1–1.5, more usually 0.2–0.4N.

As a protein releasing agent, various conventional additives may be employed in effective amounts. Known additives for thyroxine release from proteins, particularly thyroxine binding prealbumin and thyroxine binding globulin, include diphenyl hydantoin, barbital, naphthalene sulfonic acid and Releasin[R]. The preferred releasing agent is salicylate. When an hydroxylated aromatic carboxylic acid is employed, it will be in an amount sufficient to provide from about 0.5–5, preferably from about 1–4mg/ml of the hydroxylated aromatic carboxylic acid.

The amounts employed in the combined reagent solution can vary widely, since they can be diluted prior to use and then will be further diluted upon combination with the sample. The weight ratios, where the materials are combined in a single sample, will be about 5–20:1, preferably about 10:1, of α-cyclodextrin to the aromatic carboxylic acid, particularly salicylate. The amount of base employed will be determined by the final dilution to be employed. Therefore, most reagent solutions employed will generally be from about 0.25–2N, preferably from about 0.25–0.75N, in hydroxyl and preferably about 0.5N. The preferred bases, are the alkali metal bases, particularly lithium, sodium and potassium hydroxide, more particularly sodium hydroxide. In view of the basic nature of the solution, the salicylate will be present as the alkali metal salt in solution.

While each of the individual reagents can be added to the serum sample, preferably a single reagent solution is employed to minimize errors of measurement. Normally, the serum sample will not be diluted prior to use.

The values reported are based on undiluted serum, whole blood normally not being employed.

Assuming a single reagent solution is employed having the appropriate concentrations to provide the final concentration in the serum sample, the method will combine the reagent solution with the serum sample at moderate temperatures, normally from about 15°–40° C, preferably ambient temperatures of from about 15°–25° C, and the mixture will be allowed to incubate. The time for the incubation can be relatively short, usually not less than one minute and as a matter of convenience, generally not more than thirty minutes, more usually not more than about 15 minutes, generally being from about 5–15 minutes, and preferably about 10 minutes. At the end of this time, the sample may then be combined with the appropriate working solutions for the assay.

In carrying out an assay in accordance with the previously indicated U.S. patent application Ser. No. 644,408, a 50µl sample is combined with 50µl of a reagent solution which is 0.5N sodium hydroxide, 5 weight percent α-cyclodextrin and 5mg/ml salicylate. The mixture is allowed to stand at room temperature for 10 minutes. At this time, one ml of the antibody solution containing NAD is added and the mixture allowed to sit for five minutes at room temperature. To the mixture is then added 50µl of a malate dehydrogenase-thyroxine conjugate plus 500µl of buffer including malate and the mixture incubated for five minutes at 37° C. Readings are then taken at 15 minute intervals. For comparison purposes, similar runs are carried out with base only and with base and α-cyclodextrin. A number of commercial competitive protein binding (CPB) kits were obtained and tested with and without additives. (The kits tested were Amersham-Searle's Thyopac-4 CPB; Abbott's Tetrasorb$^R$ CPB; and Nuclear Medical Laboratory's Tetratab$^R$ CPB). The following table indicates the correlation between the homogeneous enzyme immunoassay and a radioimmunoassay technique unaffected by lipids which were used to measure serum samples from 30 or more patients.

|  | no additive | α-cyclodextrin added | α-cyclodextrin + salicylate |
|---|---|---|---|
| correlation coeff. | .87 | .94 | .99 |
| slope | .737 | .79 | 1.03 |
| intercept | 24.3 | 7.6 | −1.53 |

In another test, two commercial CPB kits were tested, which with 100µg/ml oleate added to a serum sample showed an increase in the thyroxine value of 20ng/ml, while at 200µg/ml oleate, the thyroxine level increased by more than 50ng per ml in some cases. These levels are reasonable levels of free fatty acid to be found in serum. However, when α-cyclodextrin was added to the fatty acid samples, at a concentration in the sample of 2.5 weight percent, the interference was eliminated.

It is evident from the above results, that alkaline α-cyclodextrin by itself, and particularly in combination with salicylate, greatly enhances the reliability and accuracy of thyroxine determinations. By employing a simple treatment step, dependable values can be obtained which correlate well between various methods of determination. In addition, the reagents employed do not interfere with the reagents subsequently employed in the determination of the thyroxine, nor do they affect the thyroxine itself.

Although the foregoing invention has been described in some detail by way of illustration and example for purposes of clarity of understanding, it will be obvious that certain changes and modifications may be practiced within the scope of the appended claims.

What is claimed:

1. A composition useful for the treatment of serum prior to thyroxine determination comprising an alkaline aqueous solution having α-cyclodextrin and salicylate in a weight ratio of about 5–20:1.

2. A composition according to claim 1 wherein the alkaline solution has an hydroxyl concentration in the range of about 0.25–2N.

3. A composition according to claim 2, wherein said weight ratio of α-cyclodextrin to salicylate is about 10:1 and said hydroxyl concentration is in the range from about 0.25–0.75N.

4. In a method for carrying out a competitive protein binding assay or a homogeneous enzyme immunoassay for polyiodothyronine in serum, the improvement which comprises adding to said serum prior to said determination, cyclodextrin to provide a final concentration 0.1–5 weight percent cyclodextrin.

5. A method according to claim 4, wherein said cyclodextrin is alpha, and a base and salicylate are added to said serum to provide a final concentration in said serum of about 0.1–1.5N hydroxide and about 0.5 to 5 mg/ml of salicylate.

6. A method according to claim 5, wherein the hydroxide is present in from 0.2–0.4N, the α-cyclodextrin is present in from about 1.5–4 weight percent and the salicylate is present in from about 1–4mg/ml.

7. A method according to claim 5 including the step of incubating the sample after addition of said base, α-cyclodextrin and salicylate.

8. A method according to claim 5, wherein said method is a homogeneous enzyme immunoassay.

9. A method according to claim 5, wherein said method is a competitive protein binding assay.

10. A method according to claim 4, wherein said method is a homogeneous enzyme immunoassay.

11. A method according to claim 4, wherein said method is a competitive protein binding assay.

* * * * *